US00RE38761E

(19) United States
(12) Reissued Patent
Levitzki et al.

(10) Patent Number: US RE38,761 E
(45) Date of Reissued Patent: Jul. 19, 2005

(54) STYRYL COMPOUNDS WHICH INHIBIT EGF RECEPTOR PROTEIN TYROSINE KINASE

(75) Inventors: Alexander Levitzki, Potomac, MD (US); Chaim Gilon, Jerusalem (IL); Michael Chorev, Jerusalem (IL); Aviv Gazit, Jerusalem (IL)

(73) Assignee: Yissum Research Development Company of the Hebrew University of Jerusalem, Jerusalem (IL)

(21) Appl. No.: 08/324,167

(22) Filed: Oct. 14, 1994

Related U.S. Patent Documents

Reissue of:
(64) Patent No.: 5,217,999
Issued: Jun. 8, 1993
Appl. No.: 07/856,849
Filed: Mar. 24, 1992

U.S. Applications:
(63) Continuation of application No. 07/515,602, filed on Apr. 27, 1990, now abandoned, which is a continuation-in-part of application No. 07/287,908, filed on Dec. 21, 1988, now abandoned.

(30) Foreign Application Priority Data

Dec. 24, 1987 (IL) ..... 84937
Nov. 10, 1988 (IL) ..... 88354

(51) Int. Cl.[7] ..... A61K 31/535; A61K 31/44; A61K 31/38; A61K 31/16

(52) U.S. Cl. ..... 514/231.5; 514/231.8; 514/232.2; 514/235.5; 514/239.5; 514/354; 514/355; 514/448; 514/415; 514/617; 514/619; 514/620; 514/621; 514/625; 514/626; 514/629; 514/599; 514/657; 514/414; 514/418; 514/764; 514/751

(58) Field of Search ..... 514/231.5, 231.8, 514/232.2, 235.5, 239.5, 354, 355, 448, 415, 617, 619, 620, 621, 625, 626, 629, 599, 657, 414, 418, 764, 751

(56) References Cited

U.S. PATENT DOCUMENTS 3,149,148 A 9/1964 Kladko et al. ..... 260/465
3,527,785 A 9/1970 Ozaki et al. ..... 260/465
4,064,266 A 12/1977 Birchall et al. ..... 424/304

FOREIGN PATENT DOCUMENTS

EP 0 339 671 11/1989
EP 0 403 238 12/1990
JP SHO 62-39558 2/1987
NZ 148038 6/1969

OTHER PUBLICATIONS

*Chemical Abstracts*, vol. 111, abstract No. 187005f, 1989.*

Shiraishi et al, *Chemical Abstracts*, vol. 106, No. 24, abstract No. 201758; 1987, p. 356.*

Chem. Abst. 111–187005f (1989).*

P. Yaish, A. Gazit, C. Gilon and A. Levitzki, *Science*, 242, pp. 933–935 (Nov. 11, 1988).

A. Gazit, P. Yaish, C. Gilon and A. Levitzki, *J. Med. Chem.* 32, pp. 2344–2352 (Oct., 1989).

T. Shiraishi, K. Kameyama, N. Imai, T. Domoto, I. Katsumi and K. Watanabe, *Chem. Pharm. Bull.*, 36(3) pp. 974–981 (1988).

T. Shiraishi, T. Domota, N. Imai, Y. Shimada and K. Watanabe, *Biochemical and Biophysical Research Communications*, 147(1), pp. 322–328 (Aug. 31, 1987).

E.M. Gal, F. Fung and D.M. Greenberg, *Cancer Research*, vol. 12, pp. 565–572 (1952).

I. Katsumi, *Chem. Pharm. Bull.*, vol. 34(1), pp. 1619–1627.

E. Gal, F. Fung and D. Greenberg, *Cancer Research*, vol. 12, pp. 574–579 (1952).

* cited by examiner

*Primary Examiner*—Rebecca Cook
(74) *Attorney, Agent, or Firm*—Winston & Strawn LLP

(57) ABSTRACT

A method of inhibiting cell proliferation in a patient suffering from such disorder comprising administering to said patient an effective amount of a composition comprising, in admixture with a pharmaceutically acceptable carrier, a compound, or a pharmaceutically acceptable salt thereof, which is a substituted styrene compound which can also be a naphthalene, an indane or a benzoxazine; including nitrile and molononitrile compounds, and pharmaceutical compositions comprising, in admixture with a pharmaceutically acceptable carrier, a pharmaceutically-effective amount of such compound.

32 Claims, 4 Drawing Sheets

SUBSTITUENTS

| COMPOUND | $R_3$ | $R_4$ | $R_5$ | $R_6$ | $R_7$ | $R_2$ | $R_1$ | Kinh μM |
|---|---|---|---|---|---|---|---|---|
| A | II | H | OH | H | H | $CO_2H$ | H | 1000 |
| B | II | H | OH | H | H | $CO_2H$ | $CO_2H$ | 500 |
| C | II | OH | OH | H | H | $CO_2H$ | H | 150 |
| D | II | OH | H | H | OH | CN | $CO_2H$ | 24 |
| E | II | H | OH | OH | H | $CO_2H$ | CN | 18 |
| F | II | H | OH | OH | H | CN | CN | 11 |
| G | II | $OHC_3$ | OH | OH | H | CN | CN | 2 |
| H | II | H | OH | OH | H | $CONH_2$ | CN | 2.3 |
| I | II | H | OH | OH | H | $CSNH_2$ | CN | 0.85 |

STYRYL COMPOUNDS WHICH INHIBIT EGF RECEPTOR PROTEIN TYROSINE KINASE

Matter enclosed in heavy brackets [ ] appears in the original patent but forms no part of this reissue specification; matter printed in italics indicates the additions made by reissue.

CROSS-REFERENCE TO RELATED APPLICATION

This is a continuation of application(s) Ser. No. 07/515,602 filed on Apr. 27, 1990, now abandoned which is a continuation-in-part of U.S. application Ser. No. 07/287,908, filed Dec. 21, 1988 now abandoned.

FIELD OF THE INVENTION

This invention relates to the inhibition of cell proliferation. More specifically, this invention relates to the use of low molecular weight styryl compounds in inhibiting cell proliferation, including compounds which are useful protein tyrosine kinase (PTK) inhibitors.

Normal cellular reproduction is believed to be triggered by the exposure of the cellular substrate to one or more growth factors, examples of which are insulin, epidermal growth factor (EGF) and platelet-derived growth factor (PDGF). Such growth factors are typically specific for corresponding growth factor receptors which are imbedded in and which penetrate through the cellular membrane. The initiation of cellular reproduction is believed to occur when a growth factor binds to the corresponding receptor on the external surface of the cellular membrane. This growth factor-receptor binding alters the chemical characteristics of that portion of the receptor which exists within the cell and which functions as an enzyme to catalyze phosphorylation of either an intracellular substrate or the receptor itself, the latter being referred to as autophosphorylation. Examples of such phosphorylation enzymes include tyrosine kinases, which catalyze phosphorylation of tyrosine amino acid residues of substrate proteins.

Many diseased states are characterized by the uncontrolled reproduction of cells. These diseased states involve a variety of cell types and include disorders such as leukemia, cancer, psoriasis, atherosclerosis and restenosis injuries. The inhibition of tyrosine kinase is believed to have utility in the control of uncontrolled cellular reproduction, i.e., cellular proliferative disorders.

Initiation of autophosphorylation, i.e., phosphorylation of the growth factor receptor itself, and of the phosphorylation of a host of intracellular substrates are some of the biochemical events which are involved in mitogenesis and cell proliferation. Autophosphorylation of the insulin receptor and phosphorylation of substrate proteins by other receptors are the earliest identifiable biochemical hormonal responses.

Elimination of the protein tyrosine kinase (PTK) activity of the insulin receptor and of the epidermal growth factor (EGF) receptor by site-directed mutagenesis of the cellular genetic material which is responsible for generation of insulin and EGF results in the complete elimination of the receptors' biological activity. This is not particularly desirable because insulin is needed by the body to perform other biological functions which are not related to cell proliferation. Accordingly, compounds which inhibit the PTK portion of the EGF receptor at concentrations less than the concentrations needed to inhibit the PTK portion of the insulin receptor could provide valuable agents for selective treatment of cell proliferation disorders.

Currently the chemotherapy of cancer makes use of inhibitors of DNA synthesis (e.g. adriamycin, fluorouracil) and compounds which disrupt the cytoskeleton (vinblastine). These compounds are highly toxic since their inhibitory activity is not limited to cancer cells, with the distinction, however, that tumor cells are more readily attacked by the aforesaid inhibitors because these cells divide more rapidly and their DNA metabolism is consequently more active. A few types of cancers are treated with specific hormone derivatives. These cases, however, are the exception and the chemotherapeutic treatment for the majority of the various types of cancer is non-specific.

In the early 1980's it became apparent that 20 to 30 percent of cancers express characteristic oncogenic products which are growth factor receptors or their mutated homologs, and which exhibit PTK activity. The PTK activity is intrinsic to the receptor or its oncogene homolog and influences the cell proliferation via its PTK domain. Furthermore, each of these receptors (normal or mutated) exhibits a characteristic PTK activity with a distinct substrate specificity. One of these receptors is the epidermal growth factor (EGF) receptor and its oncogenic homolog V-ERB-B.

REPORTED DEVELOPMENTS

As a result of the above-described developments regarding the PTK activity of growth factor receptors, it has been proposed to treat cancer by means of various chemical substances capable of inhibiting the PTK activity of EGF. See, for example, Japanese patent Nos. 62-39523, 62-39558, 62-42923 and 62-42925. For example, aforementioned Japanese Laid-open Patent No. SHO 62-39558 discloses α-cyano-2,5-dihydroxycinnamamide as the active compound in compositions effective as PTK inhibitors.

The use of cinnamal malononitrile and various benzylidene malononitrile compounds as tumor growth inhibitors is disclosed in Gal et al., Studies on the Biological Action of Malononitriles. I. The Effect of Substituted Malononitriles on the Growth of Transplanted Tumors in Mice, Cancer Research, 12:565–72, 1952.

It has been reported that the most potent inhibitors of EGF receptors inhibit EGF-induced proliferation of A431/clone 15 cells with little or no effect on the proliferation of such cells when induced by other growth factors. It has been reported also that erbstatin inhibits the autophosphorylation of the EGF receptor in membranes of A431 cells. Low concentrations of erbstatin are required to inhibit EGF receptor autophosphorylation, whereas much higher concentrations of erbstatin are required to inhibit cyclic adenosine 3',5'-monophosphate (cAMP)-dependent protein kinase.

SUMMARY OF THE INVENTION

In accordance with the invention described and claimed in aforementioned application Ser. No. 07/287,908, there is provided therein a pharmaceutical composition containing as an active ingredient a compound of the general formula I

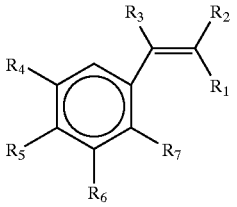

wherein:

$R_1$ and $R_2$ are each independently —CN, —$CONH_2$ or —COOH or one of $R_1$ and $R_2$ may be —$CSNH_2$ or, when $R_1$ is —CN, $R_2$ can also be the group —$C(NH_2)$=$C(CN)_2$;

$R_3$ is —H, —$CH_3$ or —OH; and $R_4$, $R_5$, $R_6$ and $R_7$ are each independently —H, —OH, $C_{1-5}$ alkyl, $C_{1-5}$ alkoxy, —$NH_2$, —CHO, halogen, —$NO_2$ or —COOH, or $R_4$ and $R_5$ together may represent a group —O—$CH_2$—)—;

provided that: (a) when $R_4$ and $R_7$ are each —OH, when $R_3$, $R_5$ and $R_6$ are each —H and when one of $R_1$ and $R_2$ is —CN, then other of $R_1$ and $R_2$ cannot be —$CONH_2$; and (b) when $R_3$ and $R_7$, are each —H, when $R_5$ is —OH and when $R_4$ and $R_6$ are both —H or both $C_{1-5}$ alkyl, then $R_1$ is —CN and $R_2$ is —CN or the group —$C(NH_2)$=$C(CN)_2$; or a pharmaceutically acceptable salt thereof.

Upon further analysis, there is provided, in accordance with the disclosure of the aforementioned parent application, a novel pharmaceutical composition containing as an active ingredient a compound described by formula I above, or a pharmaceutically acceptable salt thereof, wherein:

$R_1$ and $R_2$ are each independently —CN, —$CONH_2$ or —COOH or one of $R_1$ and $R_2$ may be —$CSNH_2$ or, when $R_1$ is —CN, $R_2$ can also be the group —$C(NH_2)$=$C(CN)_2$;

$R_3$ is —H, —$CH_3$ or —OH; and $R_4$, $R_5$, $R_6$ and $R_7$ are each independently —H, —OH, $C_{1-5}$ alkyl, $C_{1-5}$ alkoxy, —$NH_2$, —CHO, halogen, —$NO_2$ or —COOH;

provided that: (a) when $R_4$ and $R_7$ are each —OH, when $R_3$, $R_5$ and $R_6$ are each —H and when one of $R_1$ and $R_2$ is —CN, then the other of $R_1$ and $R_2$ cannot be —$CONH_2$; (b) when $R_1$ and $R_2$ are each —CN, then at least one of $R_4$, $R_5$, $R_6$ and $R_7$ is —$NH_2$, —CHO, or —COOH; and (c) when $R_3$ and $R_7$ are each —H, when $R_5$ is —OH and when $R_4$ and $R_6$ are both $C_{1-5}$ alkyl, then $R_1$ is —CN and $R_2$ is —$C(NH_2)$=$C(CN)_2$.

There is also provided, in accordance with the aforementioned parent application, a method of inhibiting cell proliferation in a patient suffering from such disorder comprising administering to said patient a pharmaceutical composition as described above.

In accordance with the present invention, there is provided a method of inhibiting cell proliferation in a patient suffering from such disorder comprising administering to said patient an effective amount of a composition comprising, in admixture with a pharmaceutically acceptable carrier, a compound, or a pharmaceutically acceptable salt thereof, selected from the group consisting of (A) a substituted styrene compound having the formula

II

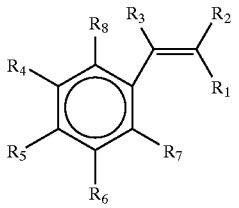

wherein:

one of $R_1$ and $R_2$ is alkyl, —H, —CN, —OH, —COOR, —CONRR or —CSNRR;

the other of $R_1$ and $R_2$ is alkyl, —H, —CN, —OH, —COOR, —CONRR, —CSNRR, —CHO, —$CONHR_9$, —$CONHCH_2CN$, —CH=$C(CN)_2$, —$C(NH_2)$=$C(CN)_2$, —NHCHO,

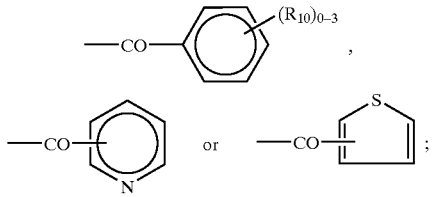

wherein $R_1$ and $R_2$ are not both alkyl, —H, —CN or —OH;

R is alkyl or —H;

$R_3$ is alkyl, —H, —CN, —OH, —COOR, —CONRR, —CSNRR, —$CH_2CN$ or —CH=C(CN)$CONH_2$;

$R_4$, $R_5$, $R_6$ and $R_8$ are each independently alkyl, —H, —CN, halo, —OR, —CHO, —COOH, —NRR, —$NO_2$, —$NHCOCH_3$, —SR, —CH=CHCOOH, —$NHCO(CH_2)_2$COOH or morpholino;

$R_3$ and $R_7$ together may be —$CH_2CH_2$—, —$CH_2CH_2CH_2$—or, starting from $R_3$, —CONH—;

$R_9$ is —$NH_2$, —$CONH_2$,

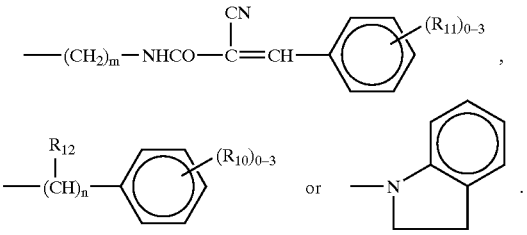

$R_{10}$ is alkyl, halo, —OR, —COOR or —$NO_2$;

$R_{11}$ is alkyl, —CN, halo, —OR, —CHO, COOH, —NRR, —$NO_2$, —$NHCOCH_3$, —SR, —CH=CHCOOH, —NHCO$(CH_2)_2$COOH or morpholino;

$R_{12}$ is alkyl, —H, halo, —OR or —COOR;

n is 0 to about 6; and m is 2 to about 10;

provided that when each of $R_4$ and $R_7$ is —OH, when each of $R_3$, $R_5$, $R_6$ and $R_8$ is —H, and when one of $R_1$ and $R_2$ is —CN, then the other of $R_1$ and $R_2$ is not —$CONH_2$; and also provided that when one of $R_1$ and $R_2$ is —CH=$C(CN)_2$, at least one of $R_3$, $R_4$, $R_5$, $R_6$ and $R_8$ is not —H;

(B) an α-substituted benzylidene malononitrile compound having the formula

III

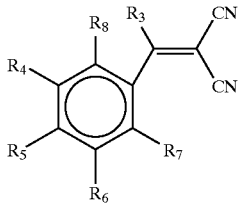

wherein:

$R_3$ is alkyl, —CN, —OH, —COOR, —CONRR, —CSNRR, —$CH_2$ CN or —CH═C(CN)$CONH_2$;

R is alkyl or —H; and $R_4$, $R_5$, $R_6$, $R_7$ and $R_8$ are each independently alkyl, —H, —CN, halo, —OR, —CHO, —COOH, —NRR, —$NO_2$, —$NHCOCH_3$, —SR, —CH═CHCOOH, —NHCO$(CH_2)_2$ COOH or morpholino;

(C) an α-unsubstituted benzylidene malononitrile compound having the formula

IV

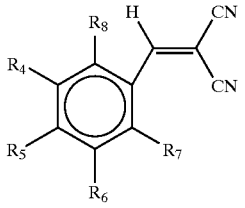

wherein:

at least one of $R_4$, $R_5$, $R_6$, $R_7$ and $R_8$ is $C_2$to about $C_6$ alkyl, —CN, —CHO, —COOH, —NHR, —SR, —CH═CHCOOH, —NHCO$(CH_2)_2$COOH or morpholino;

the remainder of $R_4$, $R_5$, $R_6$, $R_7$ and $R_8$ are each independently alkyl, —H, —CN, halo, —OR, —CHO, —COOH, —NRR, —$NO_2$, —$NHCOCH_3$, —SR, —CH═CHCOOH, —NHCO$(CH_2)_2$COOH or morpholino; and R is alkyl or —H; and (D) a bicyclic benzylidene malononitrile compound having

V

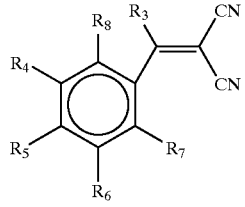

wherein:

$R_3$ and $R_7$ together are —$CH_2CH_2$—, —$CH_2CH_2CH_2$— or, starting from $R_3$, —CONH—;

$R_4$, $R_5$, $R_6$ and $R_8$ are each independently alkyl, —H, —CN, halo, —OR, —CHO, —COOH, —NRR, —$NO_2$, —$NHCOCH_3$, —SR, —CH═CHCOOH, —NHCO$(CH_2)_2$ COOH or morpholino; and R is alkyl or —H.

It should be understood that formulae II, III, IV and V above encompass within their description compounds which are common to the description of the present application and the description of the aforementioned '908 parent application and compounds which are first disclosed in the present application.

Another aspect of the present invention relates to pharmaceutical compositions comprising, in admixture with a pharmaceutically acceptable carrier, a pharmaceutically-effective amount of a compound within the scope of formula II, III or V above, and within the scope of formula IV provided that when $R_5$ is —OH and when one of $R_4$ or $R_6$ is halo, then the other of $R_4$ and $R_6$ is not tert-alkyl.

Compounds within the scope of the present invention have a specific affinity toward the substrate site of the tyrosine kinase domain of EGF receptors, inhibit EGF receptor kinase more than they inhibit PDGF receptor kinase and also effectively inhibit EGF-dependent autophosphorylation of the receptor.

DETAILED DESCRIPTION OF THE INVENTION

Figure 1:
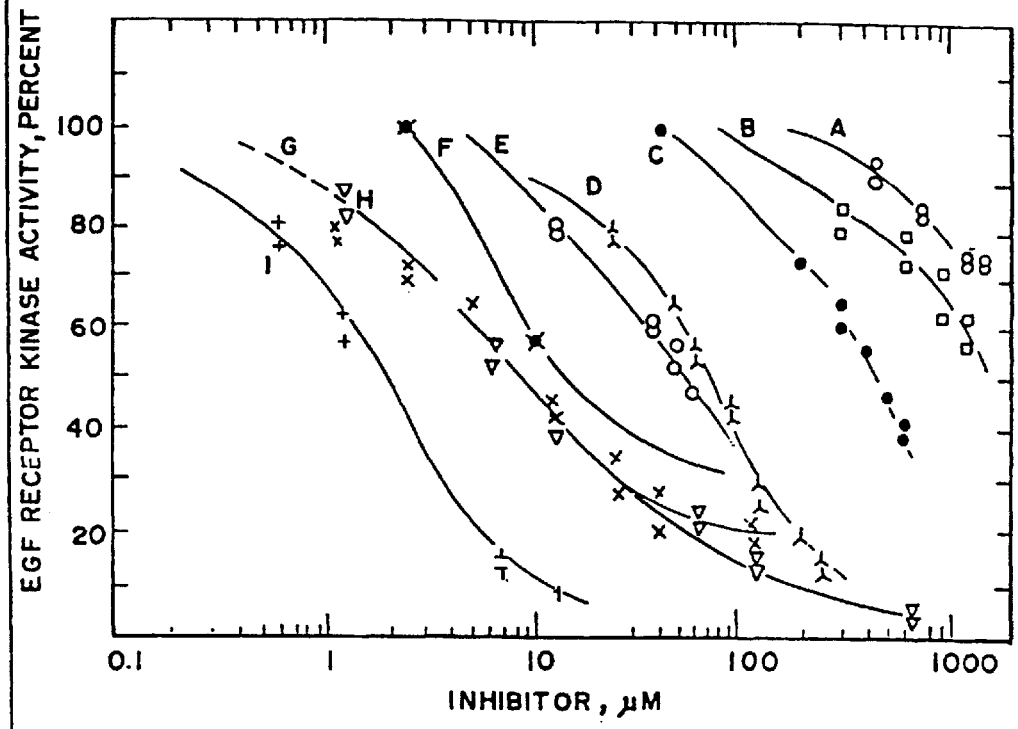
FIG. 1 is a graphical representation of the activity of isolated EGFR kinases (given in percent of the total kinase activity) plotted against the concentrations in μM of 12 different inhibitors.

As employed above and throughout the disclosure, the following terms, unless otherwise indicated, shall be understood to have the following meanings:

"Alkyl" means a saturated aliphatic hydrocarbon which may be either straight- or branch-chained containing from about 1 to about 6 carbon atoms.

"Lower alkyl" means an alkyl group as above, having 1 to about 4 carbon atoms which may be straight- or branch-chained such as methyl, ethyl, propyl, isopropyl, butyl, isobutyl, sec-butyl or tert-butyl.

"Alkoxy" means an alkyl-oxy group in which "alkyl" is as previously described. Lower alkoxy groups are preferred. Exemplary groups include methoxy, ethoxy, n-propoxy, i-propoxy and n-butoxy.

"Acyl" means an organic radical derived from an organic acid, a carboxlyic acid, by the removal of its acid hydroxyl group. Preferred acyl groups are lower alkyl carboxylic acid groups such as acetyl and propionyl. Benzoyl is also preferred.

"Halo" means a halogen. Preferred halogens include chloride, bromide and fluoride.

It is believed that therapeutically useful PTK inhibiting compounds should be competitive with the substrate of EGF receptor tyrosine kinase (EGFRK) and not with adenosine triphosphate (ATP). The PTK inhibitors quercetin and genistein, which compete with ATP, inhibit other protein kinases and as a result are highly cytotoxic. As a test of selectivity, compounds which inhibit EGFRK better than they inhibit insulin receptor kinase (IRK) and/or PDGF receptor kinase are of considerable value.

It is theorized that solubility of the compounds of the present invention both in water and in mildly hydrophobic solvents will enhance the probability that they traverse the cell membrane. Various insoluble compounds, however, have exhibited significant EGFRK inhibition in in vitro testing.

DISCLOSURE OF THE PARENT APPLICATION

Aforementioned application Ser. No. 07/287,908, the parent of this application, discloses, as a preferred class of compounds useful as the active ingredient in the pharmaceutical composition aspects of that invention, those compounds described by formula I above in which at least one of $R_1$ and $R_2$ is —CN cis to the phenyl moiety of said formula, particularly those in which $R_4$ and $R_5$ are hydroxy groups, $R_6$ is hydrogen or hydroxy and $R_3$ and $R_7$ are hydrogens. Especially preferred pharmaceutical compositions are disclosed therein as those containing as an active ingredient a compound, or a pharmaceutically acceptable salt thereof, selected from:

α-hydroxy-3,4,5-trihydroxybenzylidene malononitrile; 3-methoxy-4,5-dihydroxybenzylidene malononitrile α-cyano-3,4-dihydroxycinnamthioamide; α-cyano-3,4-dihydroxy cinnamamide;

3,5-di-tert butyl-4-hydroxybenzylidene malononitrile;

4-formylbenzylidene malononitrile;

3,4-methylenedioxy-6-nitrobenzylidene malononitrile;

3,4-dihydroxybenzylidene malononitrile;

γ-cyano-β-amino-3,4-dihydroxycinnamal malononitrile;

γ-cyano-β-amino-3,4,5-trihydroxycinnamal malononitrile;

γ-cyano-β-amino-3,4-dihydroxy-5-methoxycinnamal malononitrile;

γ-cyano-β-amino-3,4-dihydroxy-5-bromocinnamal malononitrile; and

γ-cyano-β-amino-3-hydroxy-4-nitrocinnamal malononitrile;

In accordance with another aspect of the invention disclosed and claimed in the aforementioned parent application, there are also provided compounds of formula I above, and pharmaceutically acceptable salts thereof, selected from:

α-hydroxy-3,4,5-trihydroxybenzylidene malononitrile;

α-cyano-3,4-dihydroxycinnamthioamide;

4-formylbenzylidene malononitrile;

3,4-methylenedioxy-6-nitrobenzylidene malononitrile;

γ-cyano-β-amino-3,4-dihydroxycinnamal malononitrile;

γ-cyano-β-amino-3,4,5-trihydroxycinnamal malononitrile;

γ-cyano-β-amino-3,4-dihydroxy-5-methoxycinnamal malononitrile;

γ-cyano-β-amino-3,4-dihydroxy-5-bromocinnamal malononitrile; and

γ-cyano-β-amino-3-hydroxy-4-nitrocinnamal malononitrile.

PREFERRED COMPOUNDS USEFUL IN PRACTICING THE PRESENT INVENTION

A preferred class of compounds useful in the practice of the present invention includes those compounds comprising (A) one or more cyano groups attached to the ethylene portion of the styryl compound, for example, styryl and cinnamilidene nitriles and benzylidene and cinnamal malononitriles; and/or (B) one or more substituents on the phenyl portion of the styryl compound, for example, alkyl, cyano, halo, hydroxy, alkoxy, formyl, amino, alkylamino and nitro.

A preferred class of compounds useful in the practice of the present invention can also be described as including compounds selected from the group consisting of (A) those described by Formula II above where:

$R_1$ is —CN, —COOR, —CONRR or —CSNRR;

$R_2$ is —H, —CN, —COOR, —CONRR, —CSNRR, —$CONHR_9$ or

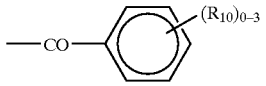

wherein $R_1$ and $R_2$ are not both —CN;

R is alkyl or —H;

$R_3$ is —H;

$R_4$, $R_5$, $R_6$, $R_7$ and $R_8$ are each independently alkyl, —H, halo or —OR;

$R_3$ and $R_7$ together may be —$CH_2CH_2$—, —$CH_2CH_2CH_2$—or, starting from $R_3$, —CONH—;

$R_9$ is —$NH_2$, —$CONH_2$;

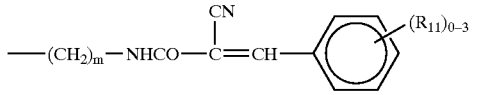

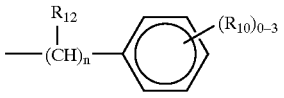

or

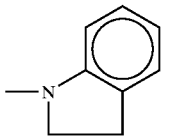

$R_{10}$ is alkyl, halo, —OH, —COOR or —$NO_2$;

$R_{11}$ is alkyl, halo or —OR;

$R_{12}$ is alkyl or —H;

n is 0 to about 4; and m is 2 to about 10;

(B) those described by formula IV above where:

at least one of $R_4$, $R_5$, $R_6$, $R_7$ and $R_8$ is $C_2$ to $C_6$ alkyl;

the remainder of $R_4$, $R_5$, $R_6$, $R_7$ and $R_8$ are each independently alkyl, —H, halo or —OR; and R is alkyl or —H; and (C) those described by formula V above where:

$R_3$ and $R_7$ together are —$CH_2CH_2$—, —$CH_2CH_2CH_2$— or, starting from $R_3$, —COHN—;

$R_4$, $R_5$, $R_6$ and $R_8$ are each independently alkyl, —H, halo or —OR; and R is alkyl or —H.

Preferred compounds described by Formula III above include (A) those compounds where:

$R_3$ is —CH, —OH, —COOR, —CONRR, —CSNRR, —$CN_2CH$ or —CH═C(CN)$CONH_2$; and (B) those compounds where:

$R_3$ is alkyl;

at least one of $R_4$, $R_5$, $R_6$, $R_7$ and $R_8$ is $C_2$ to about $C_6$ alkyl, —CN, —CHO, —COOH, —NHR, —SR, —CH═CHCOOH, —$NHCO(CH_2)_2COOH$ or morpholino; and the remainder of $R_4$, $R_5$, $R_6$, $R_7$ and $R_8$ are each independently alkyl, —H, —CH, halo, —OR, —CHO, —COOH, —NRR, —$NO_2$, —$NHCOCH_3$, —SR, —CH=CHCOOH, —$NHCO(CH_2)_2COOH$ or morpholino.

The more preferred compounds of this invention include those of Formulae VI to IX below:

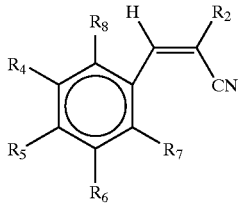

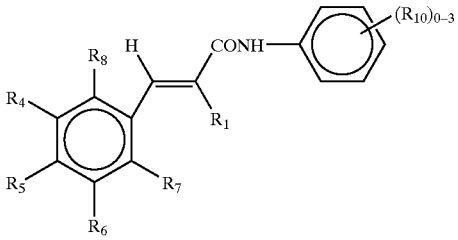

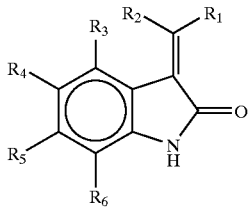

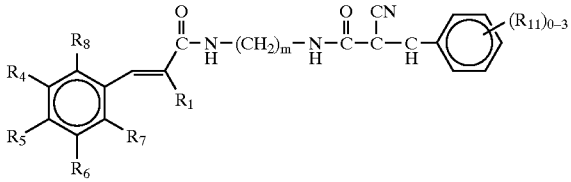

where $R_1$, $R_2$, $R_4$, $R_5$, $R_6$, $R_7$, $R_8$, $R_{10}$, $R_{11}$ and m are as described immediately above.

The most preferred compounds are described by Formulae VI, VII, VIII and IX where:

$R_1$ is —CN, —COOR, —CONRR or —CSNRR;

$R_2$ is —H, —CN, —COOR, —CONRR, —CSNRR, —$CONHR_9$ or

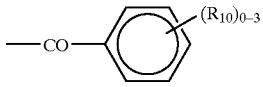

wherein $R_1$ and $R_2$ are not both —CN;

R is alkyl or —H;

$R_4$, $R_5$, $R_6$, $R_7$ and $R_8$ are each independently lower alkyl, —H, —OH, lower alkoxy or halo;

$R_{10}$ is lower alkyl or —COOR;

$R_{11}$ is lower alkyl, —OH, lower alkoxy or halo; and m is 2 to about 6.

Compounds of this invention may be useful in the form of the free base, in the form of a salt and as a hydrate. All forms are within the scope of the invention. Acid addition salts may be formed and are simply a more convenient form for use; in practice, use of the salt form inherently amounts to use of the base form. The acids which can be used to prepare the acid addition salts include preferably those which produce, when combined with the free base, pharmaceutically acceptable salts, that is, salts whose anions are nontoxic to the animal organism in pharmaceutical doses of the salts, so that the beneficial properties inherent in the free base are not vitiated by side effects ascribable to the anions. Although pharmaceutically acceptable salts of said basic compound are preferred, all acid addition salts are useful as sources of the free base form even if the particular salt per se is desired only as an intermediate product as, for example, when the salt is formed only for purposes of purification and identification, or when it is used as an intermediate in preparing a pharmaceutically acceptable salt by ion exchange procedures.

Pharmaceutically acceptable salts within the scope of the invention include those derived from the following acids: mineral acids such as hydrochloric acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid and the like.

The corresponding acid addition salts comprise the following: hydrochloride, sulfate, phosphate, sulfamate, acetate, citrate, lactate, tartarate, methanesulfonate, ethanesulfonate, benzenesulfonate, p-toluenesulfonate, cyclohexylsulfamate and quinate, respectively.

The acid addition salts of the compounds of this invention are prepared either by dissolving the free base in an aqueous or aqueous-alcohol solution or other suitable solvents containing the appropriate acid and by isolating the salt by evaporating the solution or by reacting the free base and acid in an organic solvent, in which case the salt separates directly or can be obtained by concentration of the solution.

Compounds useful in the practice of this invention can be prepared by known methods, for example, Knoevenagel condensation reactions such as those disclosed in U.S. Pat. No. 3,149,148.

Compounds of this invention may be prepared by the following reaction sequence:

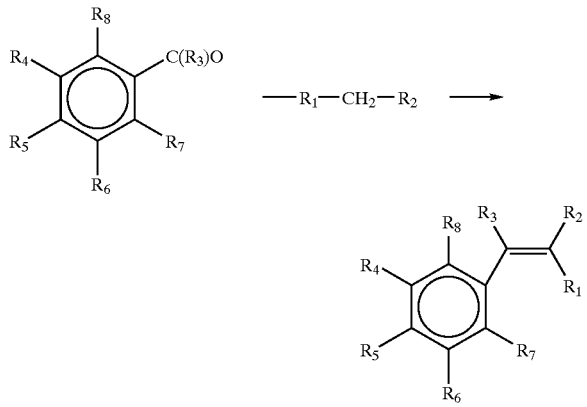

Knoevenagel condensation of a substituted benzaldehyde in a polar media with an active methylene compound of the formula $R_1CH_2R_2$ in the presence of ammonia or amines such as piperidine and raised heat results in the products of this invention. When substitution of the $R_3$ group is desired, the corresponding ketone starting material is used. Reaction temperatures in the range of 25° C. to reflux and reaction times vary depending on the materials being used in the condensation.

For example, the malonic acid derivatives of formula II above, can be prepared by reacting a corresponding substituted benzaldehyde with malononitrile to obtain the benzylidene derivatives or with malononitrile dimers to obtain the cinnamal derivatives. The reaction is generally carried out in a suitable solvent, such as ethanol or benzene, and in the presence of a catalyst, e.g., piperidine, pyridine or β-alanine Alternatively, a suitably substituted benzoyl chloride can be reacted with malononitrile in the presence of an amine in a non-polar organic solvent.

Compounds of this invention are either commercially available, known in the literature or can be made by known procedures.

Various R, $R_1$, $R_3$, $R_4$, $R_5$, $R_6$, $R_7$, $R_8$ and $R_{11}$ substituents on the phenyl ring or chain can be present in the starting compound or added after formation of the condensation product by methods known in the art for substitution or conversion of one group to another. If the substituents themselves are reactive, then the substituents can themselves be protected according to the techniques known in the art. A variety of protecting groups known in the art may be employed. Examples of many of these possible groups may be found in "Protective Groups in Organic Synthesis" by T. W. Green, John Wiley and Sons, 1981. For example, nitro groups can be added to the aromatic ring by nitration and the nitro group converted to other groups, such as amino by reduction, and halo by diazotization of the amino group and replacement of the diazo group. Acyl groups can be substituted onto the aryl groups by Friedel-Crafts acylation. The acyl groups can then be transformed to the corresponding alkyl groups by various methods, including the Wolff-Kishner reduction and Clemmenson reduction. Amino groups can be alkylated to form mono- and di-alkylamino groups and mercapto and hydroxy groups can be alkylated to form corresponding ethers. Primary alcohols can be oxidized by oxidizing agents known in the art to form carboxylic acids or aldehydes and secondary alcohols can be oxidized to form ketones. Thus, substitution or alteration reactions can be employed to provide a variety of substituents throughout the molecule of the starting material, intermediates or the final product.

Compounds within the scope of the invention exhibit significant activity as protein tyrosine kinase inhibitors and possess therapeutic value as cellular antiproliferative agents for the treatment of certain conditions including, for example, psoriasis and restenosis injuries. It is expected that the invention will be particularly applicable to the treatment of atherosclerosis. With regard to the treatment of some conditions, for example, atherosclerosis, certain people may be identified as being at high risk, for example, due to genetic, environmental or historical factors. Compounds within the scope of the present invention can be used in preventing or delaying the occurrence or reoccurrence of such conditions or otherwise treating the condition.

Compounds of the present invention can be administered to a mammalian host in a variety of forms adapted to the chosen route of administration, e.g., orally or parenterally. Parenteral administration in this respect includes administration by the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation and aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 6% of the weight of the unit. The amount of active compound in such therapeutically useful compositions is such that a suitable dosage will be obtained. Preferred compositions or preparations according to the present invention are prepared so that an oral dosage unit form contains between about 1 and 1000 mg of active compound.

The tables, troches, pills, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or a pharmacologically acceptable salt can be prepared in water suitably mixed with a surfactant such as hydroxypropylcellulose. A dispersion can also be prepared in glycerol, liquid polyethylene glycols and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from the previously sterile-filtered solution thereof.

The therapeutic compounds of this invention may be administered to a mammal alone or in combination with pharmaceutically acceptable carriers. As noted above, the relative proportions active ingredient and carrier is determined by the solubility and chemical nature of the compound, chosen route of administration and standard pharmaceutical practice.

The dosage of the present therapeutic agents which will be most suitable for prophylaxis or treatment will vary with the form of administration, the particular compound chosen and the physiological characteristics of the particular patient under treatment. Generally, small dosages will be used initially and, if necessary, will be increased by small increments until the optimum effect under the circumstances is reached. The therapeutic human dosage, based on physiological studies using rats, will generally be from about 0.01 mg to about 100 mg/kg of body weight per day or from about 0.4 mg to about 10 g or and higher although it may be administered in several different dosage units from once to several times a day. Oral administration requires higher dosages.

EXAMPLES

Embodiments of the present invention are described in the following non-limiting examples which include a description of pharmacological test procedures believed to correlate to therapeutic activity in humans and other animals.

Examples 1–5 and 15 illustrate compounds which are substituted benzylidene malononitriles, that is, $R_1$ and $R_2$ are each —CN. Examples 7–9, 13 and 14 illustrate compounds, which are substituted β-amino cinnamal malononitriles, that is, $R_1$ is —CN and $R_2$ is —$C(NH_2)$=$C(CN)_2$. Examples 6, 10, 11, 16, 18 and 24 illustrate compounds wherein $R_1$ is —CN and $R_2$ is —$CONH_2$, —COOH, —$CSNH_2$, —$CONHNH_2$, —$CONHCONH_2$ and —CO—(substituted phenyl), respectively. Example 12-C is a comparative compound and illustrates a benzylidene malononitrile wherein $R_4$ and $R_5$ together are —O—$CH_2$—O—. Example 17 illustrates a compound wherein $R_1$ is —H and $R_2$ is —CH=$C(CN)_2$. Examples 19 and 22 illustrate indanes, that is, $R_3$ and $R_7$ together are —$CH_2CH_2$—. Examples 20 and 21 illustrate compounds wherein $R_2$ is —COOR. Example 23 illustrates a tetrahydronaphthalene, that is, $R_3$ and $R_7$ together are —$CH_2CH_2CH_2$—.

EXAMPLE 1

3,4-Dihydroxybenzylidene malononitrile

To 11 g (80 mmol) of 3,4-dihydroxybenzaldehyde and 5.5 g (83 mmol) of malononitrile in 40 ml of ethanol, 7 drops of piperidine were added and the mixture was heated at 70° C. for 0.5–1 hour and then poured into water. The resulting solid precipitate was separated by filtration to give 12.7 g (86% yield) of a yellow solid, m.p. 225° C.

EXAMPLES 2–4

Following the same procedure as set forth for Example 1 above, the following were prepared: Example 2, 3-methoxy-4,5-dihydroxybenzylidene malononitrile, m.p. 235° C.; Example 3, 3,5-di-tert butyl-4-hydroxybenzylidene malononitrile, m.p. 135° C.; and Example 4, 3,5-di-tert butylbenzylidene malononitrile, m.p. 95°–98° C.

EXAMPLE 5

α-Hydroxy-3,4,5-trihydroxybenzylidene malononitrile

To 2 g (30 mmol) of malononitrile and 4 ml (40 mmol) of triethylamine in 100 ml of $CH_2Cl_2$, triacetyl galloyl chloride (prepared from 7 g (24 mmol) of triacetyl gallic acid and thionyl chloride) in 50 ml $CH_2Cl_2$ was added. The resulting mixture was then stirred for two hours at room temperature, poured into 50 ml water and hydrolyzed by heating for 2 minutes at 80° C. with a solution of 2.5 g NaOH in 30 ml ethanol. The mixture was extracted with ethyl acetate and the organic extract was further worked up by washing with water, drying, filtering and evaporation. Chromatography on silica gel gave 1.5 g (29% yield) of the product as an oily solid.

EXAMPLE 6

α-Cyano-3,4-dihydroxycinnamamide

Reaction of 2.4 g (10 mmol) 3,4-dihydroxybenzaldehyde and 0.9 g (10.7 mmol) cyanoacetamide by the procedure described in Example 1 above gave 1.45 g (70% yield) of product as a yellow solid, m.p. 247° C.

EXAMPLE 7

γ-Cyano-β-amino-3,4-dihydroxycinnamal malononitrile 1.4 g (10 mmol) 3,4-Dihydroxybenzaldehyde, 1.4 g (10.6 mmol) malononitrile dimer and 0.3 g of β-alanine in 50 ml ethanol were heated at 70° C. for 40 minutes. 100 ml of water was added, the suspension cooled and a solid precipitate was filtered off, washed with water and dried to give 1.3 g (53% yield) of a yellow-orange solid, m.p. 235° C.

EXAMPLES 8 AND 9

Following the same procedure as described for Example 7 above, the following were prepared: Example 8, γ-cyano-β-amino-3,4,5-trihydroxycinnamal malononitrile, m.p. 275° C.; and Example 9, γ-cyano-β-amino-3-hydroxy-4-nitrocinnamal malononitrile, m.p. 219° C.

EXAMPLE 10

α-Cyano-3,4-dihydroxycinnamic acid (a) 2 g (15 mmol) 3,4-Dihydroxybenzaldehyde, 3 g (21 mmol) of tert-butyl cyanoacetate and 0.5 ml of piperidine in 50 ml ethanol were heated to reflux for 1 hour, poured into water, filtered, washed and dried to yield 2.5 g (yield 66%) of tert-butyl α-cyano-3,4-dihydroxycinnamate as a yellow solid.

(b) 1.6 g of the tert-butyl ester from (a) in 10 ml of trifluoroacetic acid was stirred at room temperature for 20 minutes, 50 ml of $H_2O$ was added and the cooled suspension was filtered, washed with water and dried to give 1 g (yield 85%) of product as a yellow solid, m.p. 240° C.

EXAMPLE 11

α-Cyano-3,4-dihydroxycinnamthioamide

To 0.83 g (6mmol) 3,4-dihydroxybenzaldehyde and 0.7 g (7 mmol) cyanothioacetamide in 30 ml ethanol was added 4 drops of piperidine. The mixture was refluxed for 1 hour, poured into ice water, filtered and dried, giving 0.54 g (41% yield) of an orange solid, m.p. 213° C. Calculated analysis for $C_{10}H_8N_2O_2S$: C=54.54, H=3.64, N=12.73; found: C=54.44, H=3.87, N=12.91.

EXAMPLE 12-C 3,4-Methylenedioxy-6-nitrobenzylidene malononitrile 1 g (5.1 mmol) 3,4-Methylenedioxy-6-nitrobenzaldehyde, 0.4 g (6 mmol) malononitrile and 0.2 g β-alanine in 30 ml ethanol were stirred 16 hours at room temperature, 50 ml $H_2O$ was added and the reaction mixture was filtered, giving 1 g (80% yield) of a bright yellow solid, m.p. 104° C.

EXAMPLES 13 AND 14

Following the same procedure as described in Example 12 above, the following were prepared: Example 13, γ-cyano-β-amino- 3,4-dihydroxy-5-methoxycinnamal malononitrile, m.p. 225° C.; and Example 14, γ-cyano-β-amino-3,4-dihydroxy-5-bromocinnamal malononitrile, m.p. 241° C.

EXAMPLE 15

4-Formylbenzylidene malononitrile

To 3.1 g (15 mmol) terephthalaldehyde monoethylacetal and 1.1 g (16.5 mmol) malononitrile in 30 ml ethanol were added 6 drops piperidine. After 1 hour of reflux, 50 ml of 1 N HCl was added and the reaction mixture was heated at 70° C. for 20 minutes, cooled and filtered to give 2.3 g (85% yield) of a yellow solid, m.p. 142° C.

EXAMPLE 16

3,4-Dihydroxybenzylidenecyanoacethydrazide

To 0.69 g (5 mmol) 3,4-dihydroxybenzaldehyde and 0.55 g (5.5 mmol) cyanoacethydrazide in 40 ml ethanol was added 2 drops piperidine. After 2½ hours of reflux, the reaction mixture was cooled, filtered and washed with cold ethanol to give 0.55 g (50% yield) of product, an orange solid, m.p. 220° C. (decomposition).

EXAMPLE 17

4-Methoxycinnamal malononitrile (a) To 2 g (12.6 mmol) 4-methoxycinnamonitrile in 10:10:20 ml $H_2O$:HOAc:pyridine was added 5 g (47 mmol) $NaH_2PO_2$ (hypophosphite) followed by 2 g RaNi. After stirring 3 hours at 50° C., the reaction mixture was filtered, extracted with $CH_2Cl_2$, washed with dilute HCl, washed with $H_2O$ and evaporated to give 0.7 g (35% yield) 4-methoxycinnamaldehyde, a yellow solid, m.p. 47° C.

(b) To 0.52 g (3.2 mmol) of the aldehyde from step (a) and 0.26 g (4 mmol) malononitrile in 30 ml ethanol was added 2 drops piperidine and the reaction mixture was refluxed for 40 minutes, cooled, filtered and washed with ethanol to yield 0.61 g (90% yield) of an orange solid, m.p. 160° C.

EXAMPLE 18

3,4-Dihydroxybenzylidenecyanoacetylurea

To 0.69 g (5 mmol) 3,4-dihydroxybenzaldehyde and 0.6 g (5.3 mmol) cyanoacetylurea in 40 ml ethanol was added 2 drops piperidine. The reaction mixture was refluxed for 2 hours, cooled, filtered and washed with cold ethanol to yield 0.75 g (60% yield) of a yellow-orange solid, m.p. 235° C. (decomposition).

EXAMPLE 19

5-Methoxy-1-(cyano tert-butylcarboxymethylene) indane

To 1 g (6 mmol) 5-methoxyindanone and 1.6 g (11 mmol) tert-butylcyanoacetic acid ester in 30 ml ethanol was added 0.3 g β-alanine and the reaction mixture was refluxed for 30 minutes, evaporated and chromatographed on silica gel. Recrystallization from ethanol gave 0.45 g (25% yield) of a white solid, m.p. 132° C.

EXAMPLES 20 AND 21

Following the same procedure as set forth for Example 19 above, the following were prepared: Example 20, ethyl β-(3,5-di-tert butylphenyl)propenoic acid, m.p. 62°–65° C.; and ethyl α-cyano-β-(3,5-di-tert butylphenyl)propenoic acid, m.p. 94°–96° C.

EXAMPLE 22

5,6-Dihydroxy-1,1-dicyanomethyleneindane (a) Caffeic acid, 1.7 g (9 mmol) in 60 ml ethanol with 0.2 g 5% Pd/C was hydrogenated in a Parr apparatus for 20 hours. Filtering and solvent evaporation gave 1.37 g (81% yield) of 3,4-dihydroxyphenylpropionic acid, a white solid, m.p. 125° C.

(b) The propionic acid from step (a), 2 g, in 20 ml neat liquified HF was stirred for 24 hours in a KelF system at room temperature. The HF was evaporated and a gray solid was extracted with ethyl acetate and chromatographed on silica gel to give 0.26 g (14% yield) of 5,6-dihydroxy-1-indanone, a light brown-white solid.

(c) To the indanone from step (b), 0.25 g (1.5 mmol), in 30 ml ethanol and 0.2 g (3 mmol) malononitrile was added 80 mg β-alanine and the reaction mixture was refluxed for 20 hours and evaporated to yield a yellow-brown solid, m.p. 185° C.

EXAMPLE 23

5-Hydroxy-1,1-dicyanomethylene-1,2,3,4-tetrahydronaphthalene

To 0.5 g (3 mmol) 5-hydroxytetralone and 0.4 g (6 mmol) malononitrile in 40 ml ethanol was added 4 drops piperidine. The reaction mixture was refluxed for 14 hours, $H_2O$/HCl was added, and the product was extracted with $CH_2Cl_2$., Chromatography on silica gel gave 30 mg of product, a yellow solid, m.p. 140° C.

EXAMPLE 24

α-(3,4-Dihydroxystyryl)-4-toluylacetonitrile

To 0.7 g (5 mmol) 3,4-dihydroxybenzaldehyde and 0.8 g (5 mmol) toluylacetonitrile in 40 ml ethanol were added 4 drops piperidine and the reaction mixture was refluxed for 1½ hours and cooled. 100 ml $H_2O$ and 5 ml HCl were added and the product was extracted with $CH_2Cl_2$ and triturated with $CCl_4$ to give 0.4 g (28% yield) of product, a yellow solid, m.p. 172° C.

EXAMPLE 25

N-Phenyl-α-cyano-3,4-dihydroxycinnamamide

Following the procedure as set forth in Example 6 above, N-phenylcyanoacetamide was condensed with 3,4-dihydroxybenzaldehyde to yield the title compound, m.p. 258° C.

EXAMPLE 26

α-Cyano-β-(3,5-di-tert butylphenyl) propenethioamide

Following the procedure as set forth in Example 11 above, cyanothioacetamide was condensed with 3,5-di-tert butylbenzaldehyde to yield the title compound, m.p. 172°–174° C.

All compounds gave correct analytical and spectroscopic data.

EFGR INHIBITION TESTS

Tests on extracted EGF Receptors

EGF receptors were prepared from A431 cells (obtained from the ATCC) and PTK activity of these receptors was assayed as described by S. Braun, W. E. Raymond and E. Racker, J. Biol. Chem. 259, 2051–2054 (1984). Various compounds useful in practicing the invention were tested for their inhibitory capacity on the EGF-receptor kinase activity, using the assay described above. FIG. 1 demonstrates characteristic results using 10 compounds. The assay conditions were as described above using 0.125 mg of copoly $Glu^6Ala^3Tyr^1$. Dissociation constants were calculated from the inhibition curves and are indicated for each formula in FIG. 1.

Table 1 below summarizes the results of the above-described assay, and shows KInh, the dissociation constant of the PTK-inhibitor complex, as expressed in μM units. The different KInh values were determined by the analysis according to Dixon.

TABLE 1

| Example | KInh, μmol |
|---|---|
| 1 | 11 ± 0.1 |
| 2 | 2.2 ± 0.3 |
| 5 | 4.5 |
| 6 | 3.5 ± 0.6 |
| 7 | * |
| 8 | * |
| 9 | * |
| 10 | 23.6 |
| 11 | 0.85 |
| 13 | * |
| 14 | * |
| 15 | 20 |

*non-competitive inhibitor

The results of this assay indicate that compounds of the present invention competitively inhibit EGF receptor kinase at the substrate site of the tyrosine kinase domain of EGF receptors.

Figure 2A:
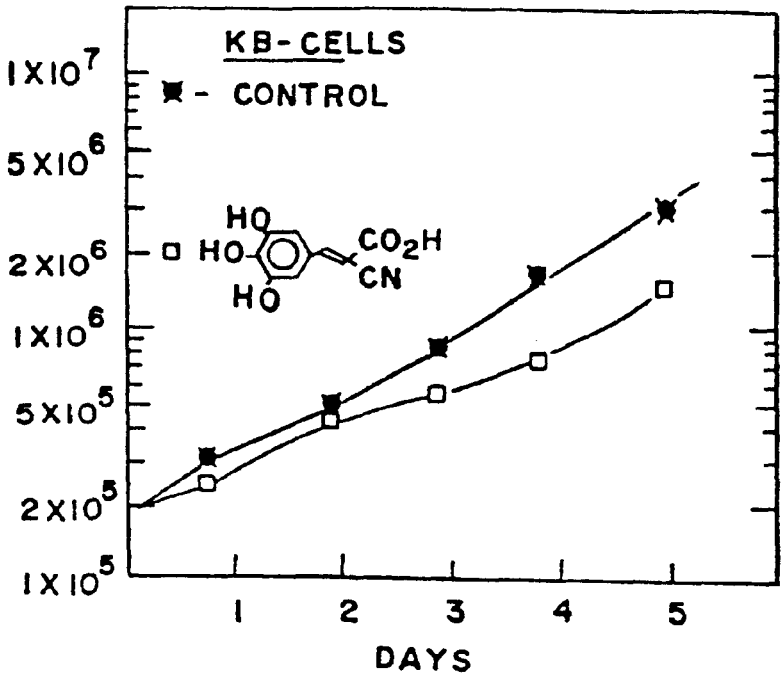
FIGS. 2a and 2b are graphical representations of the inhibitory effect of two pairs of tested compounds on the rate of the growth of KB and A431 cells respectively, the number of cells being plotted against time (in days).
Figure 2B:
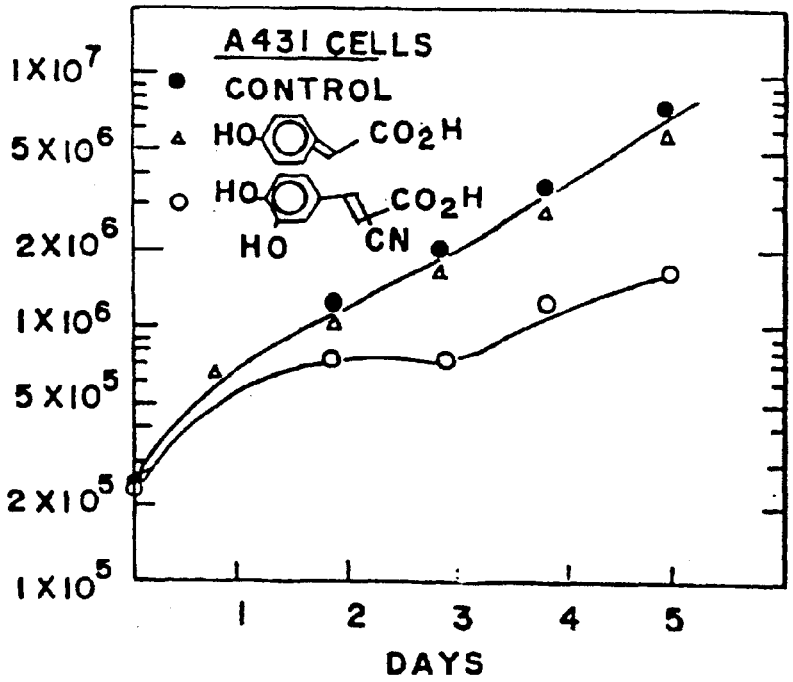
Figure 3:
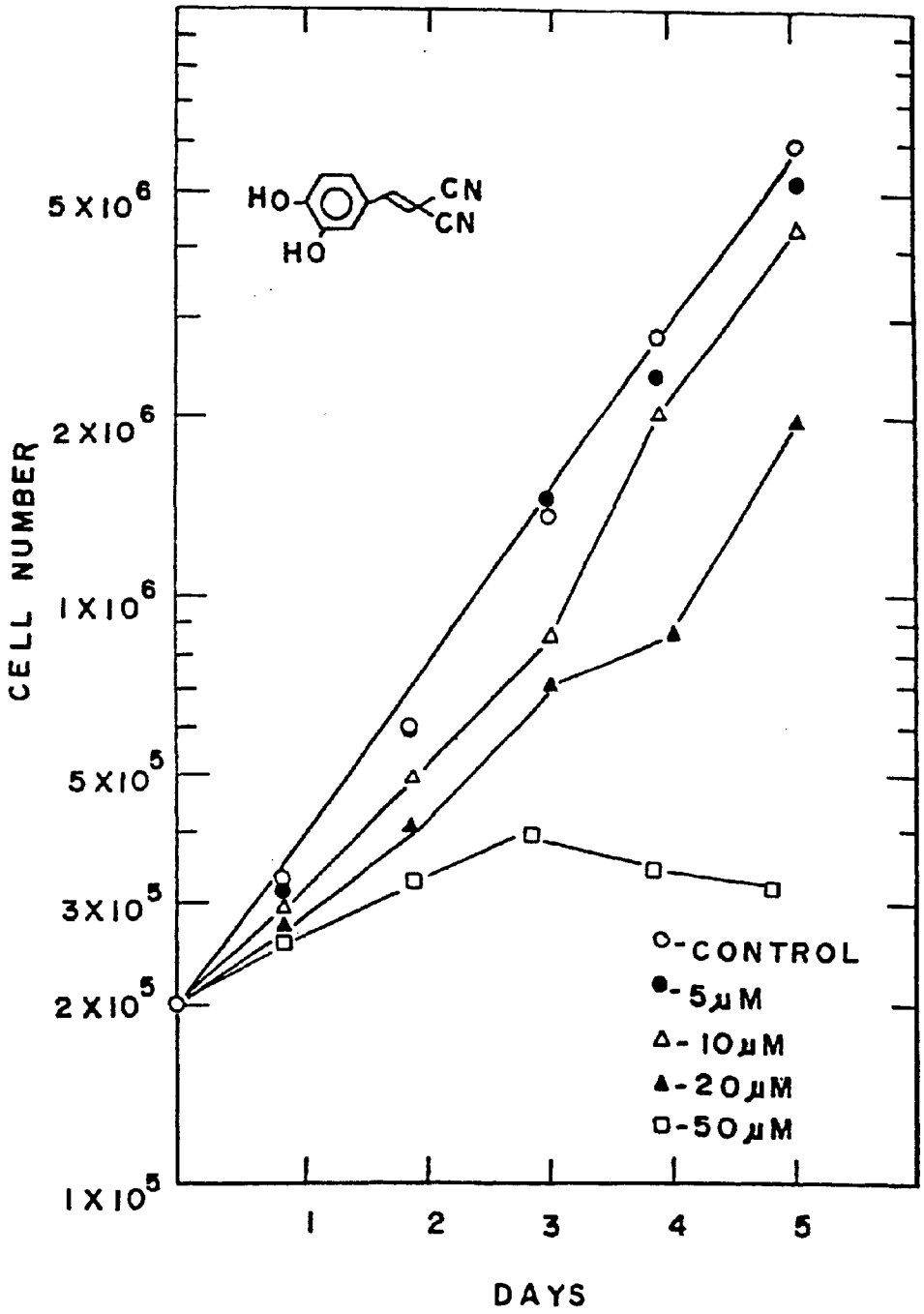
FIG. 3 is a graphical representation of the inhibition of A431 cell growth as a function of various concentrations (in μM) of the inhibitor "compound 2" according to the invention.
Figure 4A:
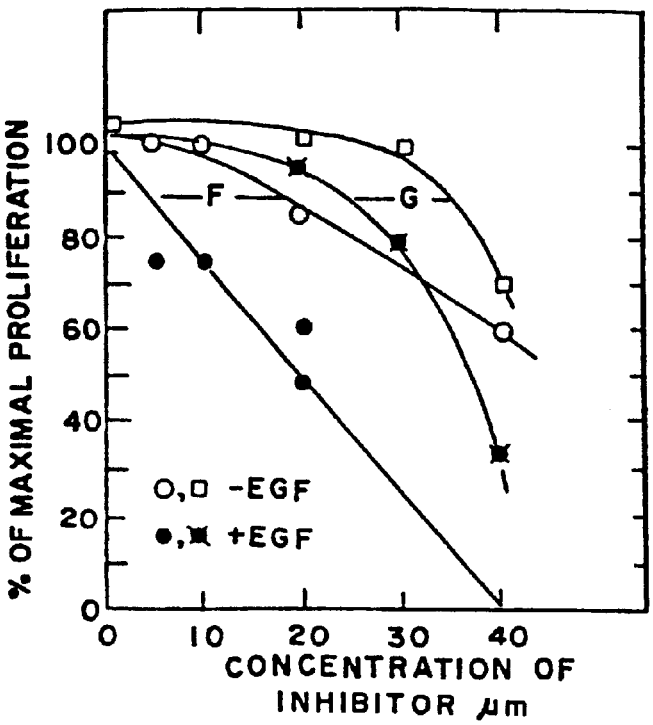
FIGS. 4a and 4b are graphical representations of the inhibitory effect of two pairs of tested compounds on the rate of the EGF-dependent proliferation of A431/clone 15 cells, with FIG. 4a depicting inhibition effects of compounds found to inhibit EGF-dependent growth preferentially and FIG. 4b depicting inhibition effects of compounds found to inhibit EGF-dependent growth exclusively.
Figure 4B:
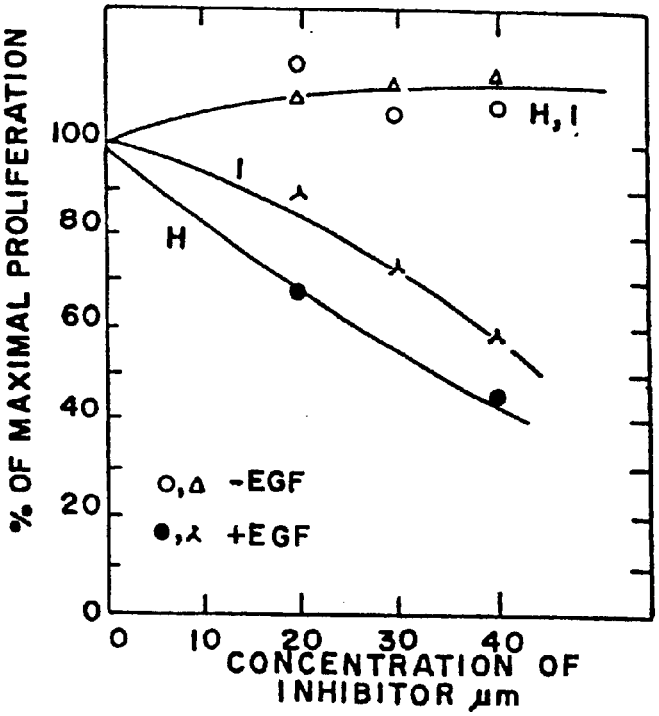

Tests on Cells in Tissue Culture a) A431 cells and KB cells express EGF receptors on their cell surface and their growth rate depends on the presence of growth factors in the medium. These cells were seeded and grown as described in O. Kashles and A. Levitzki, Biochem. Pharmacol., 35, 1531–1536 (1987). The compounds, the formulae of which are given in FIG. 2, were added to the medium at a cell concentration of about $2\times10^5$ cells/well. The inhibitor was added to the medium 1 hour after seeding. The medium volume in each well was 1 ml and the concentration of inhibitor therein 20 μM. Every 24 hours cells were counted and fresh medium with inhibitor was applied to the remaining wells. The growth curves were determined in 24-well Costar dishes.

b) Some of the compounds according to the present invention are exclusive inhibitors to EGF-dependent growth of cells and others are preferential inhibitors to such growth. Examples of the former are depicted in FIG. 4b and of the latter in FIG. 4a. In the experiment depicted in these Figures, 25,000 cells per well were placed in a 24 well plate (Costar) supplied with Dulbecco medium containing 10% foetal calf serum, with 10 ng/ml EGF (filled symbols, and ) ●, ■ and ▲) or with no added EFG (open symbols ○, □ and Δ). EGF receptor kinase inhibitors at various were added to the cells two hours after plating. The medium containing the inhibitors was replaced with fresh inhibitor-containing medium every other day. On the fifth day, the number of cells in the presence of EGF and in the absence of EGF was determined. In FIGS. 4a and 4b "100%" refers to the number of cells in the absence of inhibitor for each mode of cell growth (without EGF: 100,000±10,000 cells; with EGF: 260,000±30,000 cells for seven experiments). The filled symbols in FIGS. 4a and 4b refer to inhibition of EGF-stimulated growth, whereas the open symbols depict inhibition of EGF-independent growth. Each experimental point represents the average of triplicate determination where the variance was less than 5 percent. The compound numbers refer to compounds in FIG. 1.

Compounds of this invention are subjected to various biological tests, the results of which correlate to useful cellular antiproliferative activity. These tests are useful in determining EGF receptor kinase and insulin receptor kinase inhibition activities of the compounds disclosed herein.

EGF-Receptor Purification

EGF-receptor purification is based on the procedure of Yarden and Schlessinger. A431 cells are grown in 80 $cm^2$ bottles in confluency ($2\times10^7$ cells per bottle). The cells are washed twice with PBS and harvested with PBS containing 1.0 mmol EDTA (1 hour at 37° C.), and centrifuged at 600 g for 10 minutes. The cells are solubilized in 1 ml per $2\times10^7$ cells of cold solubilization buffer (50 mmol Hepes buffer, pH 7.6, 1% Triton X-100, 150 mmol NaCl, 5 mmol EGTA, 1 mmol PMSF, 50 μg/ml aprotinin, 25 mmol benzamidine, 5 μg/ml leupeptin, and 10 μg/ml soybean trypsin inhibitor) for 20 minutes at 4° C. After centrifugation at 100000g for 30 minutes, the supernatant is loaded onto a WGA-agarose column (100 μl of packed resin per $2\times10^7$ cells) and shaken for 2 hours at 4° C. The unabsorbed material is removed and the resin washed twice with HTN buffer (50 mmol Hepes, pH 7.6, 0.1% Triton X-100, 150 mmol NaCl), twice with HTN buffer containing 1 M NaCl, and twice with HTNG buffer (50 mmol Hepes, pH 7.6, 0.1% Triton X-100, 150 mmol NaCl, and 10% glycerol). The EGF receptor is eluted batchwise with HTNG buffer containing 0.5 M N-acetyl-D-glucosamine (200 μl per 2×10 cells). The eluted material is stored in aliquots at −70° C. and diluted before use with TMTNG buffer (50 mmol Tris-Mes buffer, pH 7.6, 0.1% Triton X-100, 150 mmol NaCl, 10% glycerol).

EGFR Kinase Catalyzed Phosphorylation of Poly (GAT) and its Inhibition

WGA-purified EGFR (0.25 μg/assay) is preactivated with EGF (0.85 μM) in 50 mmol Tris-Mes buffer, pH 7.6 for 20 minutes at 4° C. The assay is initiated by addition of a mixture which contains $Mg(Ac)_2$ (60 mmol), $[\gamma\text{-}^{32}P]ATP$ (125 μM, 2–5 μCi/assay), poly(GAT) (0.0625 mg/ml, 0.125 mg/ml, 0.25 mg/ml), and six concentrations of inhibitor in duplicates. The temperature of the assay is 22° C. and the production of phosphorylated copolymer is found to be linear up to 20 minutes. The PTK inhibitors tested are solubilized in water or a mixture of ethanol and water such that the final concentration of ethanol does not exceed 4% in the assay. Up to 4% ethanol in the assay has no effect on the EGFR kinase activity. The concentration of EGF in the assay is 300 nM in a final volume of 40 μl. After 5, 10 or 20 minutes, aliquots of 25 μl are applied onto Whatman 3-mm paper cuttings, which are then soaked in cold 10% TCA containing 0.01 M sodium pyrophosphate. After being washed overnight at 4° C., the paper cuttings are dried and counted, measuring $^{32}$P Cerenkov radiation. Concentration dependence on poly(GAT) was Michaelian with a $K_m$=0.076±0.007 mg/ml or 0.069±0.007 mmol if calculated per $Glu_6Ala_3Tyr$(GAT) unit. The EGF response for the poly(GAT) phosphorylation is graphed. The $K_m$ for ATP in the assay was found to 2.9 μM.

Time Dependence of EGF-Receptor Autophosphorylation

WGA-purified EGF receptor from A431 cells (0.5 μg/assay) is activated with EGF (800 nM) for 20 minutes at 4° C. The reaction is initiated by the addition of $Mg(Ac)_2$ (60 mmol), Tris-Mes buffer, pH 7.6 (50 mmol), and [$^{32}$P]ATP (20 μM, 5 μCi/assay). The reaction is conducted at either 4 or 15° C. and terminated by addition of sodium dodecyl sulfate (SDS) sample buffer (10% glycerol, 50 mmol Tris, pH 6.8, 5% β-mercaptoethanol, and 3% (SDS). The samples are run on a 8% SDS polyacrylamide gel (SDS-PAGE) (prepared from 30% acrylamide and 0.8% bis-(acrylamide) and contained 0.375 M Tris, pH 8.8, 0.1% SDS, 0.05% TEMED, and 0.46% ammonium persulfate). The gel is dried and autoradiography performed with Agfa Curix RP2 X-ray film. The relevant radioactive bands are cut and counted in the Cerenkov mode. The fast phase of autophosphorylation continues for another 10 minutes. The extent of phosphorylation completed in the first 10-s at 15° C. comprises ⅓ of the total autophosphorylation signal and probably reflects the phosphorylation of the first site on the receptor. The 10-s interval is therefore chosen for use in subsequent autophosphorylation experiments.

ATP and EGF Dependence of Autophosphorylation

WGA-purified EGF receptor form A431 cells (0.5 μg/assay is activated with EGF (0.85 μM) for 20 minutes at 4° C. The assay is performed at 15° C. and initiated by addition of $Mg(Ac)_2$ (60 mmol), Tris-Mes buffer, pH 7.6 (50 mmol), [$^{32}$P]ATP (carrier free, 5 μCi/assay), and increasing concentrations of nonradioactive ATP. The assay is terminated after 10-s by addition of SDS sample buffer. The samples are run on a 6% SDS polyacrylamide gel. The gel is dried and autoradiographed as described above. The relevant radioactive bands are cut and counted in the Cerenkov mode. The $K_m$ for ATP determined in this fashion is found to be 7.2 μM. With use of the 10-s assay protocol, the EGF concentration dependence of EGFRK autophosphorylation is determined.

Inhibition of Copoly($Glu_4Tyr$) Phosphorylation by Insulin-Receptor Kinase (InsRK)

Rat liver membranes are prepared from the livers of 6-week-old rats as described by Cuatrecasas. WGA-purified insulin receptor is prepared according to Zick et al. WGA-purified rat liver InsRK (1.25 μg) is preincubated with or without 330 nM insulin in 50 mmol Tris-Mes buffer, pH 7.6, for 30 minutes at 22° C. The assay is performed at 22° C. and initiated by addition of a mixture which contains $Mg(Ac)_2$ (60 mmol), $NaVO_3$ (40 μM), [β-$^{32}$P]ATP (125 μM, 3–5 μCi/assay), and poly(GT), [poly($Glu_4Tyr$)] at three concentrations: whenever an inhibitor is tested, it is added at the proper concentration. The final concentration of insulin in the assay is 125 nM. The total volume of the assay is 40 μl. After 20 minutes, aliquots of 30 μl are applied on Whatman 3-mm paper and soaked in cold 10% TCA, containing 0.01 M sodium pyrophosphate. After being washed overnight, the papers are dried and counted, measuring Cerenkov radiation. The InsRk-catalyzed phosphorylation of poly(GT) obeys Michaelis-Menten kinetics.

Inhibition of EGFR Autophosphorylation

A431 cells were grown to confluence on human fibronectin coated tissue culture dishes. After washing 2 times with ice-cold PBS, cells were lysed by the addition of 500 μl/dish of lysis buffer (50 mmol Hepes, pH 7.5, 150 mmol NaCl, 1.5 mmol $MgCl_2$, 1 mmol EGTA, 10% glycerol, 1% triton X-100, 1 mmol PMSF, 1 mg/ml aprotinin, 1 mg/ml leupeptin) and incubating 5 minutes at 4° C. After EGF stimulation (500 μg/ml 10 minutes at 37° C.) immunoprecipitation was performed with anti EGF-R (Ab 108) and the autophosphorylation reaction (50 μl aliquots, 3 μCi [γ-$^{32}$P ATP) sample was carried out in the presence of 2 or 10 μM of compound, for 2 minutes at 4° C. The reaction was stopped by adding hot electrophoresis sample buffer. SDS-PAGE analysis (7.5% gel) was followed by autoradiography and the reaction was quantitated by densitometry scanning of the x-ray films.

Inhibition of Cell Proliferation as Measured by Inhibition of DNA Synthesis

Cells were seeded at $1\times10^5$ cells per well in 24-well Costar dishes pre-coated with human fibronectin (by incubating for 30 minutes at room temperature with 10 μg/0.5 ml/well). The cells were grown to confluence for 2 days. The medium was changed to DMEM containing 0.5 calf serum for 36–48 hours and the cells were then incubated with EGF (Toyobo, New York, N.Y.) (20 ng/ml) or serum (10% calf serum) and different concentrations of the inhibitory compounds. [$^3$H]thymidine, (NEN, Boston, Ma.) was added 16–24 hours later at 0.5μCi/ml for 2 hours. TCA precipitable material was quantitated by scintillation counting (C). Results of this assay are summarized in Table II below. "$IC_{50}$," as used below, refers to the concentration of inhibitor (μM) at which [$^3$H]thymidine incorporation is halved, compared with media containing no inhibitor. As FCS contains a broad range of growth factors, the $IC_{50}$ values for EGF should be lower than for FCS, indicating that the compounds do not act as general inhibitors.

TABLE II

| Example | $IC_{50}$ - EGF | $IC_{50}$ - FCS |
|---|---|---|
| 3 | 0.1 | 0.2 |
| 21 | 20 | 120 |
| 25 | 30 | 100 |
| 26 | 20 | 100 |

These results indicate that the compounds of the invention do not inhibit a broad range of growth factor receptors.

Cell Culture

Cells termed HER 14 and K721A (=DK) were prepared by transfecting NIH3T3 cells (clone 2.2) (From C. Fryling, NCI, NIH), which lack endogenous EGF-receptors, with cDNA constructs of wild-type EGF-receptor or mutant EGF-receptor lacking tyrosine kinase activity (in which Lys 721 at the ATP-binding site was replaced by an Ala residue, respectively). All cells were grown in DMEM with 10% calf serum (Hyclone, Logan, Utah).

The results obtained by the above experimental methods evidence the useful protein tyrosine kinase inhibition properties of the compounds within the scope of the present invention.

We claim:

1. A method for inhibiting, in a patient, cell proliferation associated with a disorder selected from the group consisting of psoriasis, atherosclerosis and restenosis comprising administering to said patient an effective amount of a composition comprising, in admixture with a pharmaceutically acceptable carrier, a compound, or a pharmaceutically acceptable salt thereof, selected from the group consisting of (A) a substituted styrene compound having the formula

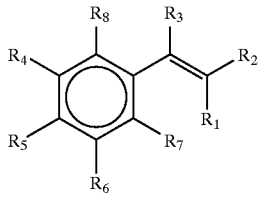

wherein:

one of $R_1$ and $R_2$ is alkyl, —H, —CN, —OH, —CONRR or —CSNRR;

the other of $R_1$ and $R_2$ is alkyl, —H, —CN, —OH, —CONRR, —CSNRR, —CONHR$_9$, —CONHCH$_2$CN, —CH═C(CN)$_2$, —C(NH$_2$)═C(CN)$_2$ or —NHCHO wherein $R_1$ and $R_2$ are not both alkyl, —H, —CN or —OH;

R is alkyl or —H;

$R_3$ is alkyl, —H, —CN, —OH, —CONRR, —CSNRR, —CH$_2$CN or —CH═C(CN)COHN$_2$;

$R_4$, $R_5$, $R_6$, $R_7$ and $R_8$ are each independently alkyl, —H, —CN, halo, —NO$_2$ or —NHCOCH$_3$;

$R_3$ and $R_7$ together may be —CH$_2$CH$_2$—, —CH$_2$CH$_2$CH$_2$—or, starting from $R_3$, —CONH—;

$R_9$ is, —CONH$_2$,

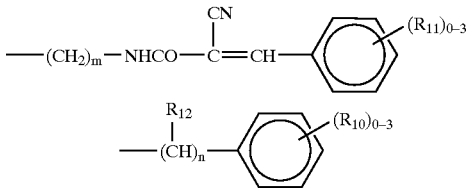

$R_{10}$ is alkyl, halo or —NO$_2$;

$R_{11}$ is alkyl, —CN, halo, —NO$_2$ or —NHCOCH$_3$;

$R_{12}$ is alkyl, —H, halo,;

n is 0 to about 6; and m is 2 to about 10, provided that when one of $R_1$ and $R_2$ is —CH═C(CN)$_2$, at least one of $R_3$, $R_4$, $R_5$, $R_6$, $R_7$ and $R_8$ is not —H;

(B) an α-substituted benzylidene malononitrile compound having the formula

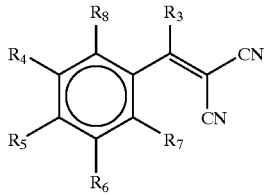

wherein:

$R_3$ is alkyl, —CN, —OH, —CONRR, —CSNRR, —CH$_2$CN or —CH═C(CN)CONH$_2$;

R is alkyl or —H; and $R_4$, $R_5$, $R_6$, $R_7$ and $R_8$ are each independently alkyl, —H, —CN, halo, —NO$_2$ or —NHCOCH$_3$;

(C) an α-unsubstituted benzylidene malononitrile compound having the formula

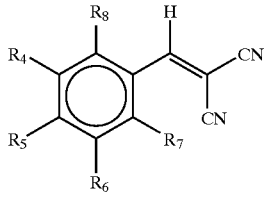

wherein:

at least one of $R_4$, $R_5$, $R_6$, $R_7$ and $R_8$ is $C_2$ to about $C_6$ alkyl or —CN;

the remainder of $R_4$, $R_5$, $R_6$, $R_7$ and $R_8$ are each independently alkyl, —H, —CN, halo, —NO$_2$ or —NHCOCH$_3$; and R is alkyl or —H; and (D) a bicyclic benzylidene malononitrile compound having the formula

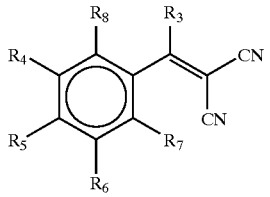

wherein:

$R_3$ and $R_7$ together are —CH$_2$CH$_2$—, —CH$_2$CH$_2$CH$_2$— or, starting from $R_3$, —CONH—; and $R_4$, $R_5R_6$ and $R_8$ are each independently alkyl, —H, —CN, halo, —NO$_2$ or —NHCOCH$_3$.

2. A method according to claim 1 wherein said compound has the formula

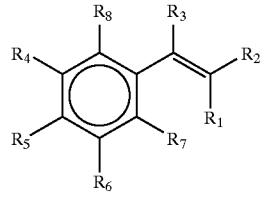

$R_1$ is —CN, —CONRR or —CSNRR;

$R_2$ is —H, —CN, —CONRR, —CSNRR or —CONHR$_9$;

wherein $R_1$ and $R_2$are not both —CN;

R is alkyl or —H;

$R_3$ is —H;

$R_4$, $R_5$, $R_6$, $R_7$ and $R_8$ are each independently alkyl, —H, or halo;

$R_3$ and $R_7$ together may be —$CH_2CH_2$—, —$CH_2CH_2CH_2$—or, starting from $R_3$, —CONH—;

$R_9$ is —$CONH_2$,

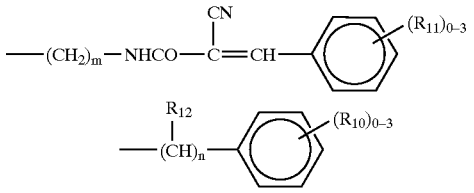

$R_{10}$ is alkyl, halo or —$NO_2$;

$R_{11}$ is alkyl or halo;

$R_{12}$ is alkyl or —H;

n is 0 to about 4; and m is 2 to about 6.

3. A method according to claim 1 wherein said compound has the formula

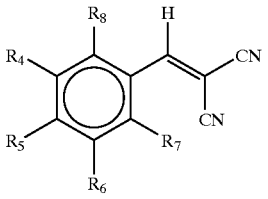

wherein:

at least one of $R_4$, $R_5$, $R_6$, $R_7$ and $R_8$ is $C_2$ to $C_6$ alkyl; and the remainder of $R_4$, $R_5$, $R_6$, $R_7$ and $R_8$ are each independently alkyl, —H or halo.

4. A method according to claim 1 wherein said compound has the formula

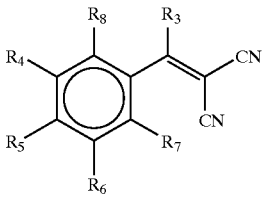

wherein:

$R_3$ and $R_7$ together are —$CH_2CH_2$—, —$CH_2CH_2CH_2$— or, starting from $R_3$, —CONH—; and $R_4$, $R_5$, $R_6$ and $R_8$ are each independently alkyl, —H or halo.

5. A method according to claim 2 wherein $R_1$ is —CN.

6. A method according to claim 2 wherein said compound has the formula

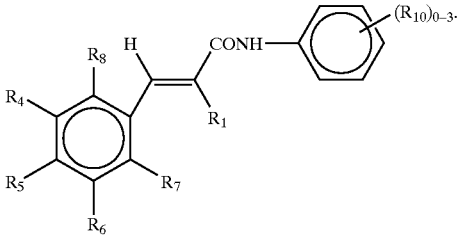

7. A method according to claim 1 wherein said compound has the formula

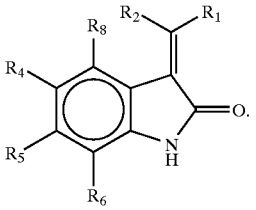

8. A method according to claim 2 wherein said compound has the formula

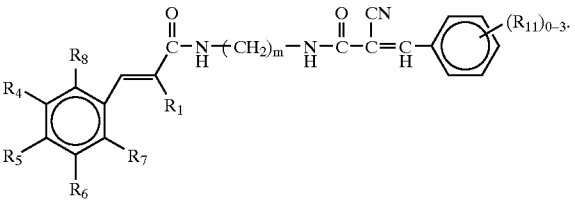

9. A method according to claim 5 wherein $R_2$ is —H, CN, —CONRR, —CSNRR or —CONHR$_9$;

wherein $R_1$ and $R_2$ are not both —CN;

R is alkyl or —H;

$R_4$, $R_5$, $R_6$, $R_7$ and $R_8$ are each independently lower alkyl, —H or halo;

$R_9$ is —$CONH_2$,

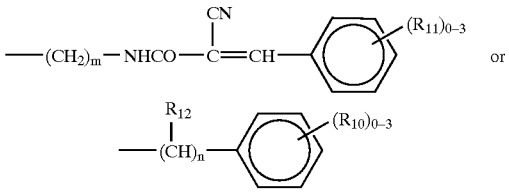

$R_{10}$ is lower alkyl;

$R_{11}$ is lower alkyl or halo; and m is 2 to about 10.

10. A method according to claim 6 wherein $R_1$ is —CN, —CONRR or —CSNRR;

R is alkyl or —H;

$R_4$, $R_5$, $R_6$, $R_7$ and $R_8$ are each independently lower alkyl, —H or halo; and $R_{10}$ is lower alkyl.

11. A method according to claim 7 wherein $R_1$ is —CN, —CONRR or —CSNRR;

$R_2$ is —H, —CN, —CONRR, —CSNRR, —CONHR$_9$;

R is alkyl or —H;

$R_4$, $R_5$, $R_6$ and $R_8$ are each independently lower alkyl, —H or halo; and $R_{10}$ is lower alkyl.

12. A method according to claim 8 wherein $R_1$ is —CN, —CONRR or —CSNRR;

R is alkyl or —H;

$R_4$, $R_5$, $R_6$ and $R_8$ are each independently lower alkyl, —H or halo;

$R_{11}$ is lower alkyl or halo; and m is 2 to about 6.

13. A method according to claim 1 wherein said compound is α-cyano-β-(3,5-di-tert butylphenyl) propenethioamide.

14. A method according to claim 1 wherein said cell proliferation condition comprises psoriasis.

15. A method according to claim 1 wherein said cell proliferation condition comprises atherosclerosis.

16. A method according to claim 14 wherein said compound is α-cyano-β-(3,5-di-tert-butylphenyl) propenethioamide.

17. A method for inhibiting, in a patient, cell proliferation associated with a disorder selected from the group consisting of psoriasis, atherosclerosis and restenosis comprising administering to said patient an effective amount of a composition comprising, in admixture with a pharmaceutically acceptable carrier, a compound, or a pharmaceutically acceptable salt thereof, selected from the group consisting of (A) a substituted styrene compound having the formula

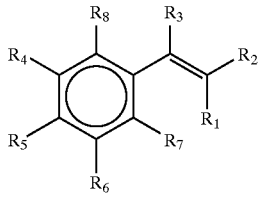

wherein:

$R_1$ and $R_2$ are each independently —CN or —$CONH_2$ or one of $R_1$ and $R_2$ may be —$CSNH_2$ or , when $R_1$ is CN, $R_2$ can also be the group —$C(NH_2)$=$C(CN)_2$, with the proviso that $R_1$ and $R_2$ are not both CN;

$R_3$ is —H, —$CN_3$ or —OH;

$R_4$, $R_5$, $R_6$ and $R_7$ are each independently alkyl of 1–5 carbons, —H, halo, or —$NO_2$; and $R_8$ is H;

(B) an α-substituted benzylidene malononitrile compound having the formula

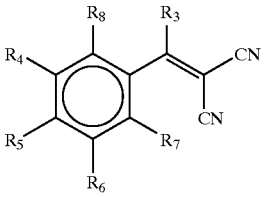

wherein:

$R_3$ is —$CH_3$ or —OH;

$R_4$, $R_5$, $R_6$ and $R_7$ are each independently alkyl of 1–5 carbons, —H, halo, or —$NO_2$; and $R_8$ is —H; or (C) an α-unsubstituted benzylidene malononitrile compound having the formula

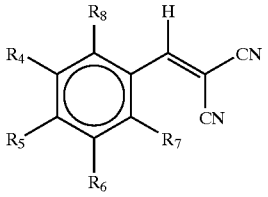

wherein:

at least one of $R_4$, $R_5$, $R_6$ and $R_7$ is alkyl or 2–5 carbons;

the remainder of $R_4$, $R_5$, $R_6$ and $R_7$ are each independently alkyl of 1–5 carbons, H, halo or —$NO_2$; and $R_8$ is —H;

or a pharmaceutically acceptable salt thereof.

18. A method according to claim 17 wherein said disorder comprises psoriasis.

19. A method according to claim 17 wherein said disorder comprises psoriasis and said compound comprises α-cyano-β-(3,5-di-tert-butylphenyl)propenethioamide.

20. A method according to claim 1 wherein said compound has the formula

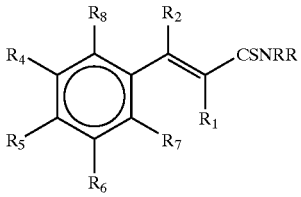

wherein:

R is alkyl or —H;

$R_1$ is —H, —CN, —OH or —CONRR;

$R_3$ is alkyl, —H, —CN or —OH;

$R_4$, $R_5$, $R_6$, $R_7$ and $R_8$ are each independently alkyl, —H, —CN or halo.

21. A method according to claim 17 wherein said compound has the formula

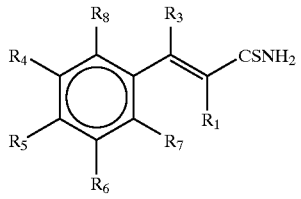

wherein:

$R_1$ is —CN or —$CONH_2$;

$R_3$ is —H, —$CH_3$ or —OH;

$R_4$, $R_5$, $R_6$ and $R_7$ are each independently alkyl of 2≧4 carbons, —H, halo or —$NO_2$; and $R_8$ is —H.

*22. A method for inhibiting, in a patient, cell proliferation associated with a disorder selected from the group consisting of psoriasis, atherosclerosis, restenosis, and leukemia comprising administering to said patient an effective amount of a composition comprising, in admixture with a pharma-* ceutically acceptable carrier, a compound, or a pharmaceutically acceptable salt thereof, comprising a substituted styrene compound having the formula

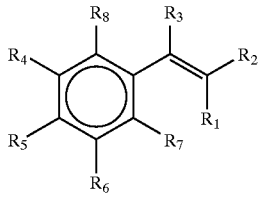

wherein:

one of $R_1$ and $R_2$ is alkyl, —H, —CN, —OH, —COOR, —CONRR or —CSNRR;

the other of $R_1$ and $R_2$ is alkyl, —H, —CN, —OH, —COOR, —CONRR, —CSNRR, —CHO, —CONHR$_9$, —CONHCH$_2$CN, —CH=C(CN)$_2$, —C(NH$_2$)=C(CN)$_2$, —NHCHO,

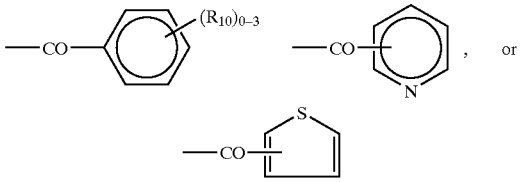

wherein $R_1$ and $R_2$ are not both alkyl, —H, —CN or —OH;

R is alkyl or —H;

$R_3$ is alkyl, —H, —CN, —OH, —COOR, —CONRR, —CSNRR, —CH$_2$CN or —CH=C(CN)CONH$_2$;

$R_4$, $R_5$, $R_6$, $R_7$ and $R_8$ are each independently alkyl, —H, —CN, halo, —OR, —CHO, —COOH, —NRR, —NO$_2$, —NHCOCH$_3$, —SR, —CH=CHCOOH, —NHCO(CH$_2$)$_2$COOH or morpholino;

$R_3$ and $R_7$ together may be —CH$_2$CH$_2$—, —CH$_2$CH$_2$CH$_2$—or, starting $R_3$, —CONH—;

$R_9$ is —NH$_2$, —CONH$_2$,

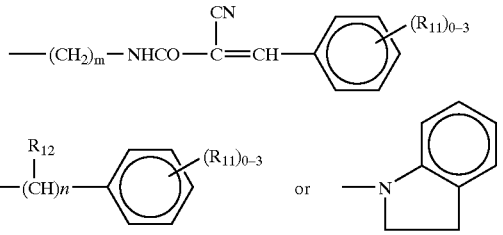

$R_{10}$ is alkyl, halo, —OR, —COOR, or —NO$_2$;

$R_{11}$ is alkyl, —CN, halo, —OR, CHO, COOH, NRR, —NO$_2$, —NHCOCH$_3$, —SR, —CH=CHCOOH, —NHCO(CH$_2$)$_2$COOH or morpholino;

$R_{12}$ is alkyl, —H, halo, —OR, or —COOR;

n is 0 or about 6; and m is 2 to about 10;

provided that when each of $R_4$ and $R_7$ is OH, when each of $R_3$, $R_5$, $R_6$, and $R_8$ is —H and when one of $R_1$ and $R_2$ is —CN, then other of $R_1$ and $R_2$ is not —CONH$_2$; and also provided that when one of $R_1$ and $R_2$ is —CH=C(CN)$_2$, at least one of $R_3$, $R_4$, $R_5$, $R_6$, $R_7$ and $R_8$ is not —H; and provided that when said $R_1$ or $R_2$ is COOR or CONRR, the other of said $R_1$ or $R_2$ is not alkyl or cyano.

23. A method for inhibiting, in a patient, cell proliferation associated with a disorder selected from the group consisting of psoriasis, atherosclerosis, restenosis, and leukemia comprising administering to said patient an effective amount of a composition comprising, in admixture with a pharmaceutically acceptable carrier, a compound, or a pharmaceutically acceptable salt thereof, comprising a substituted benzylidene malononitrile compound having the formula

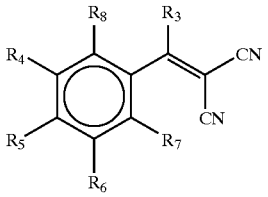

wherein:

$R_3$ is alkyl, —CN, —OH, —COOR, —CONRR, —CSNRR, —CH$_2$CN or —CH=C(CN)COHN$_2$;

R is alkyl or —H; and $R_4$, $R_5$, $R_6$, $R_7$ and $R_8$ are each independently alkyl, —H, —CN, halo, —OR, —CHO, —COOH, —NRR, —NO$_2$, —NHCOCH$_3$, —SR, —CH=CHCOOH, —NHCO(CH$_2$)$_2$COOH or morpholino.

24. A method for inhibiting, in a patient, cell proliferation associated with a disorder selected from the group consisting of psoriasis, atherosclerosis, restenosis, and leukemia comprising administering to said patient an effective amount of a composition comprising, in admixture with a pharmaceutically acceptable carrier, a compound, or a pharmaceutically acceptable salt thereof, comprising unsubstituted benzylidene malononitrile compound having the formula

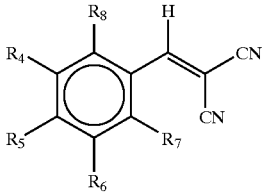

wherein:

at least one of $R_4$, $R_5$, $R_6$, $R_7$ and $R_8$ is $C_2$ to about $C_6$ alkyl, —CN, —CHO, —COOH, —NHR, —SR, —CH=CHCOOH, —NHCO(CH$_2$)$_2$COOH or morpholino;

the remainder of $R_4$, $R_5$, $R_6$, $R_7$ and $R_8$ are each independently alkyl, —H, —CN, halo, —OR, —CHO, —COOH, —NRR, —NO$_2$, —NHCOCH$_3$, —SR, —CH=CHCOOH, —NHCO(CH$_2$)$_2$COOH or morpholino; and R is alkyl or —H.

25. A method for inhibiting, in a patient, cell proliferation associated with a disorder selected from the group consisting of psoriasis, atherosclerosis, restenosis, and leukemia comprising administering to said patient an effective amount of a composition comprising, in admixture with a pharmaceutically acceptable carrier, a compound, or a pharmaceutically acceptable salt thereof, selected from the group consisting of a bicyclic benzylidene malononitrile compound having the formula

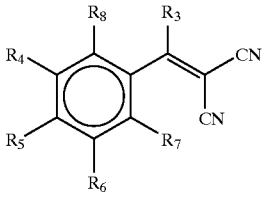

*wherein:*

*$R_3$ and $R_7$ together are —$CH_2CH_2$—, —$CH_2CH_2CH_2$— or, starting from $R_3$, —CONH—; and*

*$R_4$, $R_5$, $R_6$ and $R_8$ are each independently alkyl, —H, —CN, halo, —OR, —CHO, —COOH, —NRR, —$NO_2$, —$NHCOCH_3$, —SR, —CH═CHCOOH, —NHCO$(CH_2)_2$COOH or morpholino; and*

*R is alkyl or —H.*

*26. A method according to claim 22 wherein said compound has the formula*

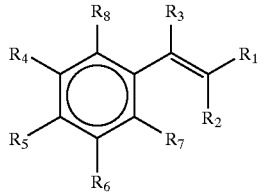

*wherein*

*$R_1$ is —CN, —COOR, —CONRR or —CSNRR;*

*$R_2$ is —H, —CN, —COOR, —CONRR, —CSNRR, —$CONHR_9$ or*

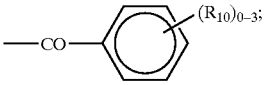

*wherein $R_1$ and $R_2$ are not both —CN;*

*R is alkyl or —H;*

*$R_3$ is —H;*

*$R_4$, $R_5$, $R_6$, $R_7$ and $R_8$ are each independently alkyl, —H, halo or —OR;*

*$R_3$ and $R_7$ together may be —$CH_2CH_2$—, —$CH_2CH_2CH_2$—or, starting from $R_3$, —CONH—; and*

*$R_9$ is —$NH_2$, —$CONH_2$,*

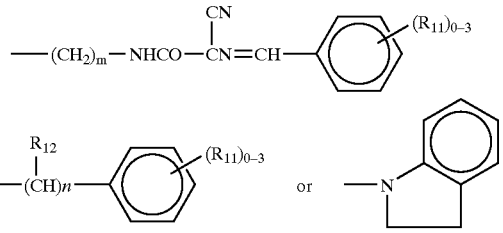

*$R_{10}$ is alkyl, halo, —OH, —COOR, or —$NO_2$;*

*$R_{11}$ is alkyl, halo or —OR;*

*$R_{12}$ is alkyl or —H;*

*n is 0 to about 4; and*

*m is 2 to about 10.*

*27. A method according to claim 22 wherein said compound has the formula*

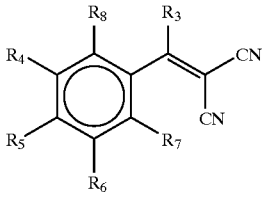

*wherein:*

*at least one of $R_4$, $R_5$, $R_6$, $R_7$ and $R_8$ is $C_2$ to $C_6$ alkyl; and*

*the remainder of $R_4$, $R_5$, $R_6$, $R_7$ and $R_8$ are each independently alkyl, —H, halo or —OR; and*

*R is alkyl or —H.*

*28. A method according to claim 22 wherein said compound has the formula*

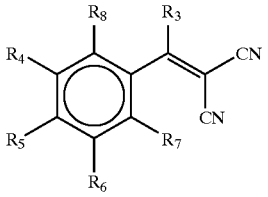

*wherein:*

*$R_3$ and $R_7$ together are —$CH_2CH_2$—, —$CH_2CH_2C$—$H_2$— or, starting from $R_3$, —CONH—; and*

*$R_4$, $R_5$, $R_6$, and $R_8$ are each independently alkyl, —H, halo or —OR; and*

*R is alkyl or —H.*

*29. A method according to claim 5, wherein*

*$R_2$ is —H, CN, —COOR, —CONRR, —CSNRR, —$CONHR_9$ or*

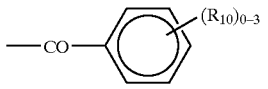

*wherein $R_1$ and $R_2$ are not both —CN;*

*R is alkyl or —H;*

*$R_4$, $R_5$, $R_6$, $R_7$ and $R_8$ are each independently lower alkyl, —H, —OH, lower alkoxy or halo;*

*$R_9$ is $NH_2$, $CONH_3$,*

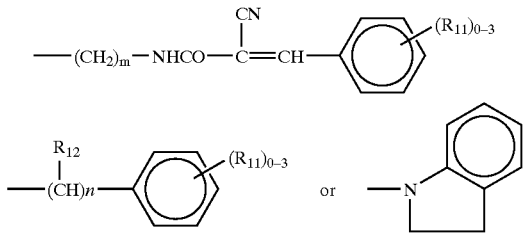

*$R_{10}$ is lower alkyl or —COOR;*

*$R_{11}$ is lower alkyl, —OH, lower alkoxy or halo; and*

*m is 2 to about 10.*

*30. A method according to claim 6 wherein*

*R1 is —CN, —COOR, —CONRR or CSNRR;*

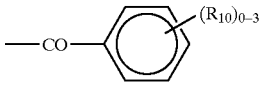

*R is alkyl or —H;*

*$R_4$, $R_5$, $R_6$, R7 and $R_8$ are each independently lower alkyl, —H, —OH, lower alkoxy or halo; and*

*$R_{10}$ is lower alkyl or —COOR.*

*31. A method according to claim 7 wherein*

*R1 is —CN, —COOR, —CONRR or CSNRR;*

*$R_2$ is —H, —CN, —COOR, —CONRR, —CSNRR, —CONHR$_9$;*

*R is alkyl or —H;*

*$R_4$, $R_5$, $R_6$, R7 and $R_8$ are each independently lower alkyl, —H, —OH, lower alkoxy or halo; and*

*$R_{10}$ is lower alkyl or —COOR.*

*32. A method according to claim 8 wherein*

*R1 is —CN, —COOR, —CONRR or CSNRR;*

*R is alkyl or —H;*

*$R_4$, $R_5$, $R_6$, R7 and $R_8$ are each independently lower alkyl, —H, —OH, lower alkoxy or halo; and*

*$R_{11}$ is lower alkyl, —OH, lower alkoxy or halo; and*

*m is 2 to about 6.*

* * * * *

UNITED STATES PATENT AND TRADEMARK OFFICE

CERTIFICATE OF CORRECTION

PATENT NO. : RE 38,761 E
DATED : July 19, 2005
INVENTOR(S) : Levitzki et al.

It is certified that error appears in the above-identified patent and that said Letters Patent is hereby corrected as shown below:

Title page,
Item [56], References Cited, OTHER PUBLICATIONS,
"T. Shiraishi et al." reference, after "T. Shiraishi" change "T. Domota" to
-- T. Domoto --.
"I. Katsumi" reference, after "*Chem. Pharm. Bull.*, vol." change "34(1)" to -- 34(4) --.

Column 26,
Line 28, in the formula change "$R_2$" to -- $R_3$ --.

Column 31,
Line 15, after "$R_4$, $R_5$, $R_6$,", change "*R7*" to -- $R_7$ --.

Column 32,
Lines 6 and 12, after "$R_4$, $R_5$, $R_6$,", change "*R7*" to -- $R_7$ --.

Signed and Sealed this

Eighteenth Day of October, 2005

JON W. DUDAS
*Director of the United States Patent and Trademark Office*